United States Patent [19]

Holm-Kennedy et al.

[11] Patent Number: 4,926,682
[45] Date of Patent: May 22, 1990

[54] VISCOSITY SENSOR

[75] Inventors: James W. Holm-Kennedy; Scot P. McArthur, both of Honolulu, Hi.

[73] Assignee: The Research Corporation of the University of Hawaii, Honolulu, Hi.

[21] Appl. No.: 201,887

[22] Filed: Jun. 3, 1988

[51] Int. Cl.$^5$ .......................................... G01N 11/00
[52] U.S. Cl. ....................................................... 73/54
[58] Field of Search .......................... 73/54; 324/61 R; 361/280, 281

[56] References Cited

U.S. PATENT DOCUMENTS

| | | | |
|---|---|---|---|
| 2,772,393 | 11/1956 | Davis | 331/65 |
| 3,278,919 | 10/1966 | Fleming | 307/308 |
| 3,500,366 | 3/1970 | Chesney et al. | 331/65 |
| 3,666,999 | 5/1972 | Moreland, Jr. et al. | 307/308 |
| 3,910,564 | 10/1975 | Graham et al. | 366/18 |
| 4,104,595 | 8/1978 | Overzet | 331/65 |
| 4,166,381 | 9/1979 | Woo | 73/54 |
| 4,310,806 | 1/1982 | Ogasawara | 331/65 |
| 4,357,834 | 11/1982 | Kimura | 331/65 |
| 4,443,754 | 4/1984 | King | 73/64 |
| 4,470,008 | 9/1984 | Kato | 307/308 |
| 4,495,821 | 1/1985 | Terhune | 73/722 |
| 4,515,015 | 5/1985 | Kuhlman | 331/65 |
| 4,604,898 | 8/1986 | Gohin et al. | 331/65 |
| 4,646,070 | 2/1987 | Yasuhara et al. | 331/65 |
| 4,733,556 | 3/1988 | Meitzler et al. | 340/631 |

FOREIGN PATENT DOCUMENTS 0047812 12/1978 Fed. Rep. of Germany .......... 73/54

OTHER PUBLICATIONS

Telephone and Telephone Exchanges, pp. 112–113.

Primary Examiner—Hezron E. Williams
Attorney, Agent, or Firm—James Creighton Wray

[57] ABSTRACT

A device for measuring the viscosity of pure and mixed fluids is described. The device is a micromechanical capacitor transducer, with a moving membrane and a stationary metal plate constituting the capacitive system. A conduit for gas flow permits the gas to fill the volume between the moving membrane and metal plate. The gas viscosity sensor is operable by applying a d.c. pulse of an a.c. electrical voltage. By electrically driving the device the conducting membrane is caused to deflect with respect to the stationary metal plate. This results in a measureable capacitance, frequency or resistance change with time. The impedance to flow determines the response time of the capacitor plate membrane displacement. Thus the viscosity of pure and mixed fluids is indicated by the transient and/or a.c. characteristics of the device capacitance.

27 Claims, 3 Drawing Sheets

VISCOSITY SENSOR

BACKGROUND OF THE INVENTION

At the present time, the general method of measuring the viscosity of gases includes the use of a vibrating resilient wire loop and use of damped oscillating discs. Another method is the use of a piezoelectric transducer to provide vibration energy thereby imparting shear waves to the surrounding fluid. An output signal provides a representation of the properties of the fluid viscosity. The disadvantages of the prior methods are due to the complexity of the apparatus and methodology used in measuring the gas viscosity and the ofen large size of the measuring appartus. Additionally, the later devices are usually not prone to manufacture using batch processing techniques, and thus tend to be costly. In large devices large fluid volumes are necessary. This latter feature tends to exclude fluid measurements where only very small samples of the fluid are available.

SUMMARY OF THE INVENTION

To overcome these shortcomings the present invention uses a micromechanical structure which consists of a small volume between two capacitor plates, where one (or both) of the plates is flexible and is displaced by the application of a step d.c. voltage, or by the application of an a.c. voltage. The said movement of said flexible capacitor plate causes a pressure differential between the small enclosed volume and that of the surroundings causing fluid to be exchanged between the capacitor volume and the surroundings by means of flow through one or more open ports connecting the capacitor fluid volume to the surroundings.

The exchange of fluid between the small capacitor fluid volume and the surroundings exhibits itself in the impedance of the capacitor structure. Said exchange is dependent upon fluid viscosity and exit/entrance port geometry. Inspection of the capacitor impedance under transient and/or a.c. operation conditions results in an accurate measurement of fluid viscosity.

The device can be fabricated from silicon material and thus is easily integrated with appropriate circuitry and easily batch processed using silicon integrated circuit technology.

The small size, low cost, electronic character, electronic integratable features and high measurement resolution of the device provide meaningful improvements over the prior art. Monitoring the capacitor impedance results in a precise measurement of the fluid viscosity. The present invention is relatively inexpensive to fabricate being integrated circuit batch processing technology. The device is also very small and can easily be used to measure the fluid properties of small volumes of gases or other fluids.

The present invention is a simple and inexpensive device which can accurately measure the viscosity of pure and mixed gases. Measurement of viscosity can also be used to determine the relative percentage mix of gas mixtures. Examples include water vapor in air and organic vapors in air. The invention can easily be driven electrically to provide capacitance impedance information which is easily related to the gas viscosity value. To achieve this purpose, the invention is provided with electrical contacts therein adapted to be used as a circuit element in a simple RC or other electrical arrangement, and to analyze said capacitor transient response or a.c. impedance response. The gas viscosity sensor may have a conducting membrane or diaphragm (of Silicon, plated Silicon, Dioxide, or any other conducting material) bonded to a second substrate (of Glass, Plastic, Silicon, or any other material) which has a second conducting metal contact (of Aluminum, Gold or any other metal) which forms one plate of a two plate capacitor. Fluid flow paths placed between the capacitor fluid volume and air external region permit gas transport between the capacitor volume and the surroundings through the path. This construction makes it possible to deflect the flexible conducting membrane with respect to a stationary metal plate by applying a voltage resulting in an electric field across two conducting plates of the capacitive system and to observe the rate of fluid flow out of (or into) the capacitor volume.

It is an object of the invention to provide a viscometer of simple, inexpensive, practical design which is constructed from relatively few components and which samples small volumes of fluid and which provides high measurement resolution.

Another object is to provide a viscometer that can be constructed with any material to form a conductive elastic membrane or diaphragm and any substrate material with metal contact pads to form a sensitive capacitive transducer.

Other objects and advantages of the invention will become more apparent from the specifications taken in conjunction with the accompanying drawings.

DETAILED DESCRIPTION OF THE INVENTION

Figure 1:
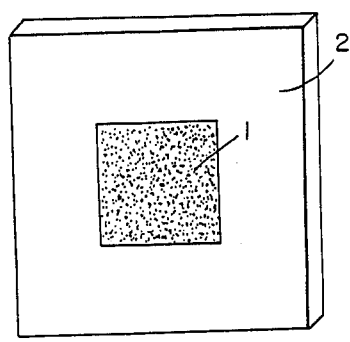
FIG. 1 is a top view of the conducting membrane suspended on all sides by the conducting substrate. The shape and size of the conducting membrane is not limited to what is illustrated.
Figure 2:
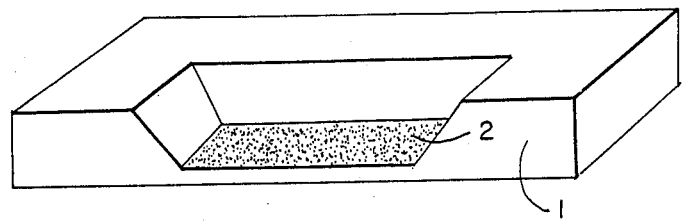
FIG. 2 is a cross-section of the conducting membrane and conducting substrate, illustrating that the thickness of the conducting membrane is much smaller than that of the supporting conducting substrate.
Figure 3:
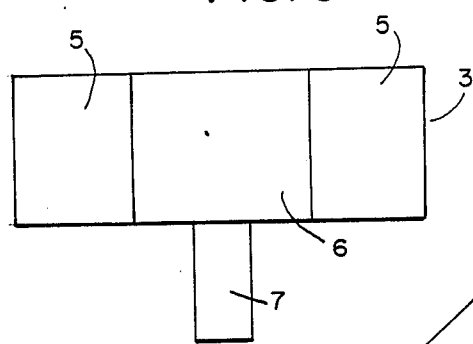
FIG. 3 is a top view of the etched pattern on the insulating substrate which forms the gap region, i.e., volume, between the capacitor plates and also forms the conduit ports and electrical interconnect to one of capacitor plates.
Figure 4:
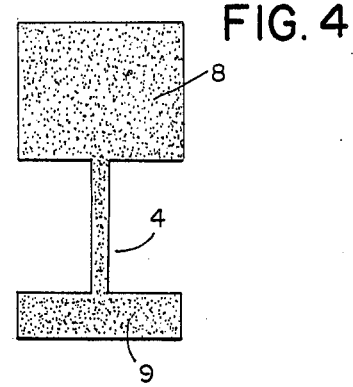
FIG. 4 is a top view of the metal pattern deposited on the insulating substrate to create the conducting metal capacitor plate and the related electrical contact pad for external electrical circuit connection.
Figure 5A:
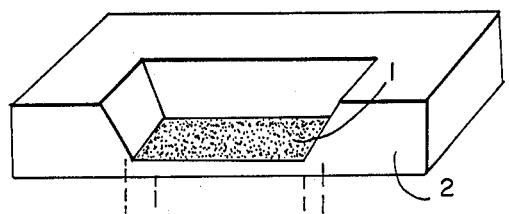
FIG. 5a illustrates the flexible conducting membrane (attached to the supporting substrate) which is placed above the insulating substrate etched well and conducting metal capacitor plate.
Figure 5A:
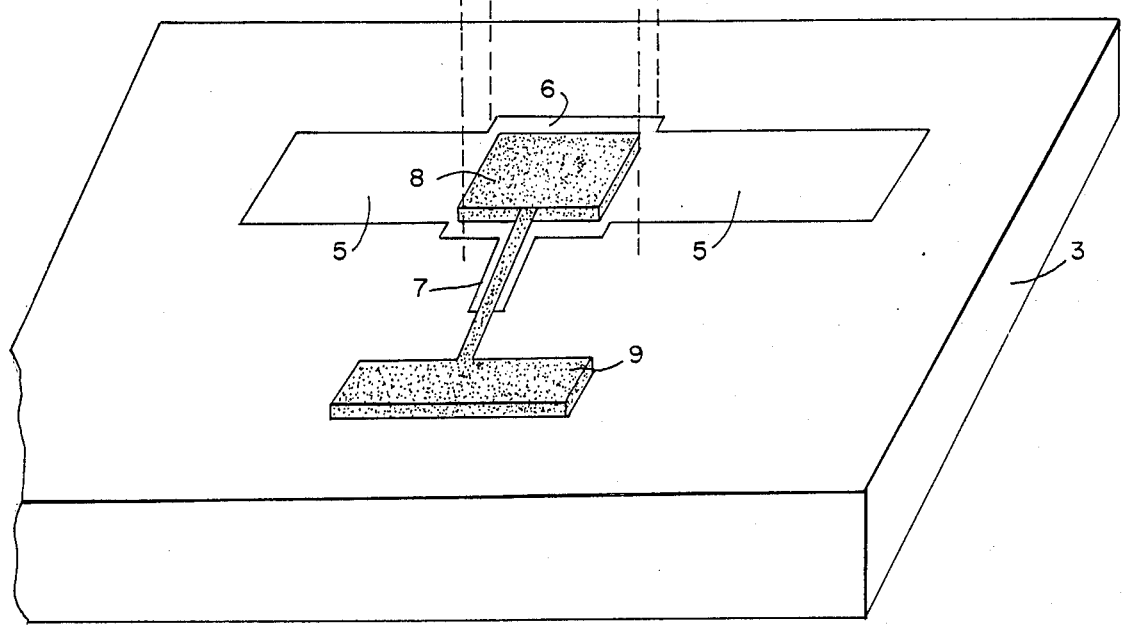
Figure 5B:
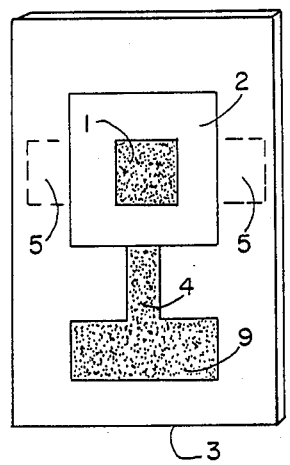
FIG. 5b is a top view of the gas viscosity sensor indicating the conducting membrane is centered above the conducting metal located in the substrate well.
Figure 6:
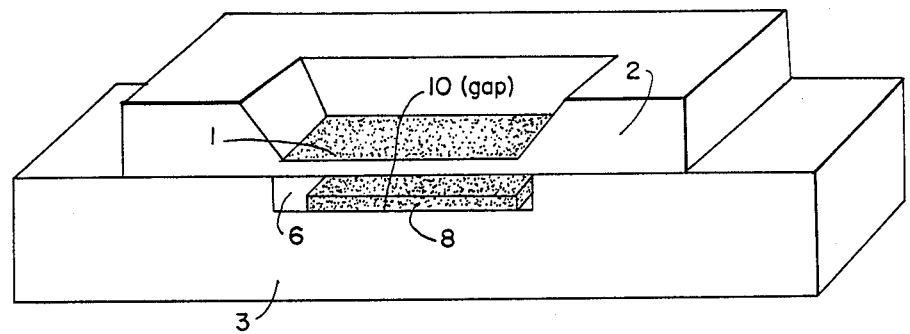
FIG. 6 is a cross-section of the gas viscosity sensor.
Figure 7:
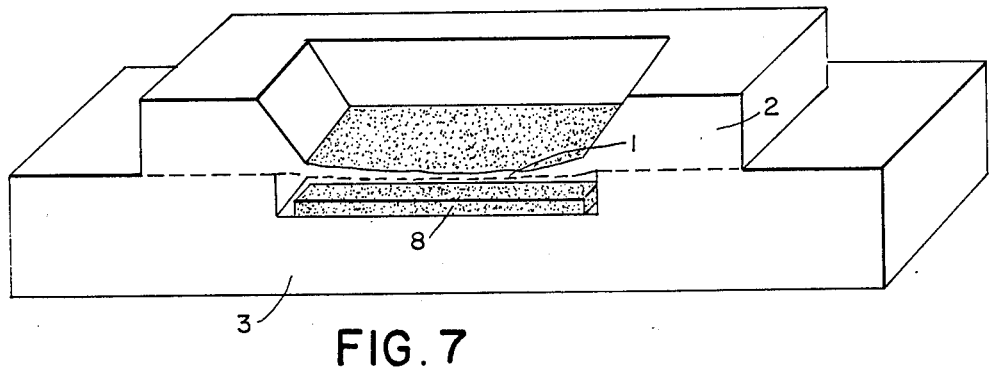
FIG. 7 is a cross-section of the gas viscosity sensor showing the displaced flexible conducting membrane.
Figure 8:
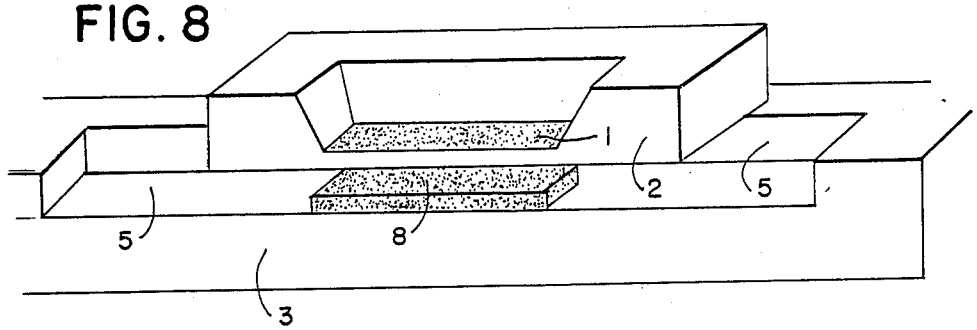
FIG. 8 is a cross-section of the gas viscosity sensor illustrating the conducting membrane parallel to the metal plate separated by the gap region and the conduit ports extending from either side.

The gas viscosity sensor of the present invention has a flexible conducting membrane 1 (FIG. 1) suspended by a surrounding substrate 2. The cross-section of the conducting membrane is given in FIG. 2. The conducting membrane 1 is very thin in comparison to supporting conducting substrate 2. Since conducting membrane 1 is very thin, it is very flexible and easily deflected by a force, such as that arising from a voltage applied across the capacitor plate. The insulating substrate 3 is fabricated by etching the recessed pattern shown in FIG. 3. The fluid conduit paths 5 (FIG. 3) extend from the membrane-metal gap to the surroundings and these entry/exit ports 5 permit the fluid (e.g., a gas) to be transported between the membrane-metal gas and the surroundings. The square area 6 is the volume between the membrane and metal pad. Outlet 7 is used as an insulated electric interconnect path to provide electrical connection 4 to the fixed plate of the capacitor 8. The metal interconnect path 4 which passes through the insulated conduit recessed into the glass is shown in FIG. 4. This conduit is sealed when desired, using an adhesive or other sealing means. Metal contact plate 8 is the stationary plate of the membrane-metal, (i.e., "parallel" plate) capacitor. Metal electrical contact pad 9 provides the external electrical connection to capacitor plate 8 via electrical interconnect 4. FIG. 5 shows the conducting substrate 2 which is supporting the conductive membrane 1 which is located above the insulating substrate 3 which has an etched well 6 into the bottom of which is placed the second conducting plate 8 of the capacitor. The device is electrically probed from metal contact pad 9 (FIG. 5b) and from the conducting substrate 2. The silicon substrate has been made conducting over much of its surface by heavy boron doping. FIG. 6 shows a cross-section of the flexible membrane capacitor gas viscosity sensor. The volume between flexible capacitor plate 1 and metal plate 8 is the gap region 10 between the "parallel" plates of the capacitor transducer system and which holds the fluid, e.g., a gas, the viscosity of which is to be measured. A cross-section showing the capacitor structure where the conducting flexible membrane is deflected by an applied voltage across the capacitor is shown in FIG. 7. Conducting membrane 1 (FIG. 7) is deflected toward stationary metal plate 8 by an applied voltage which creates an electric field between capacitor plates 1 and 8, said electric field attracting the plates towards one another. FIG. 8 is similar to FIG. 6 but also shows the gas conduit ports 5 which allow the test gas to flow in and out of the capacitor. The gas conduit ports provide for entry of the gas into the gap between conducting membrane and metal plate 8 and also provide an impedance to fluid flow. The gas or fluid between conducting membrane 1 and metal plate 8 also exits the gap through conduit port 5 when conducting membrane 1 is deflected toward metal plate 8, i.e., when the gap volume is decreased. Conduit ports 5 impede the flow of the exit gas from the capacitor gap volume due to the viscous effects of the gas. Since the gas flow out of the gap is impeded (dependent upon the gas viscosity value) the rate that conducting membrane 2 deflects (due to an applied voltage) is also impeded. The rate that conducting membrane 2 deflects due to an applied voltage is characterized by the transient response of capacitor transducer due to an applied step voltage. The features of the time dependent capacitance provide a measure of the fluids' viscosity.

Since all gases have different viscosity values, the impedance of the gas flow from the capacitor volume due to a differential pressure created by the applied step voltage force deflecting the capacitor membrane varies from gas to gas.

That is, the flow of gas through the exit port is impeded in relationship to its viscosity value. A gas or fluid with a high viscosity glows more slowly through the exit port than does gas with a lower viscosity. (The effect is similar to molasses or water flowing, due to pressure, through a garden hose. Molasses being of higher viscosity flows slower than does water, which has a lower viscosity than molasses.) The more viscous gas, the flow of which is more impeded, takes longer to flow through the exit port than does a lower viscosity gas. Thus, for the higher viscosity gas, the flexible membrane capacitor plate displaces at a slower rate than the flexible membrane displaces for a lower viscosity gas. Since the separation of the flexible membrane 2 from the fixed capacitor plate 8 determines the sensor capacitance value, the change of the sensor capacitance with time is slower for a more viscous gas than for a less viscous gas. The specific time rate of change of the capacitance with respect to time due to an applied voltage step function thus gives a measure of the viscosity of the gas. FIG. 9B illustrates the time dependent behavior of the capacitor in response to an applied step voltage $V_S$ at time $t=0$ for two different gases (gas #1 and gas #2). The value of the viscosity can be determined from the slope of the time dependent capacitance, $C(t)$, i.e., $dC(t)/dt$, at $t=0$, or from the characteristic time constant for $C(t)$ at any selected time $t_o$ where $t_o < 0$. High viscosity gases have a smaller value of $dC(t)/dt$ at $t=0$, longer time constants, and smaller relative values $c(t_o)$ at $t=t_o$ than do low viscosity gases.

The value of the viscosity can be determined via calibration of the device using reference gases of known viscosity. Alternatively, the device can be analyzed using the theory of fluid flow to provide the viscosity.

The capacitance value can be measured in a variety of ways. For example, an impedance can be measured; The frequency of an $R_{ext}C$ oscillator can be monitored (where $R_{ext}$ is an externally applied resistance); The behavior of various circuits dependent upon capacitance values can be monitored; A capacitance bridge can be used. A very convenient approach is to inspect the change in the capacitance charge $Q_c(t)=C(t)V_S$ where $V_S$ is magnitude of the applied step voltage (FIG. 9b). In this latter case, if the charge up time of the capacitance is fast compared to the gas expulsion time, monitoring $dQ/dt$ provides $dC(t)/dt$ and $C(t)$ directly, and thus constitutes a simple and straightforward method of measurement of the viscosity dependent slopes and time constants described above. The viscosity is determined empirically or using theory from the said time dependent capacitor behavior.

An alternative method of measuring the gas viscosity value is to use the same or similar device but to apply an a.c. oscillator voltage or current to the sensor capacitor. At sufficiently low frequencies of oscillation, the gas will have adequate time to enter and exit the gas port 5 linking the capacitor cavity with the external atmosphere. That is, the capacitor will follow the applied a.c. voltage in phase. At sufficiently high frequencies of applied voltage oscillation, the gas will not have the opportunity to exit or enter the gas port 5 and the flexible membrane 1 will not have sufficient time to displace significantly before the applied oscillating voltage is reversed. In this latter case, the flexible membrane will appear rigid and essentially negligible capacitance change will occur with time. When the oscillating frequency has a period approximately equal to the equivalent $R_{gas}C_{gas}$ time constant (FIG. 9c), where $R_{gas}$ represents the gas flow impedance $R_{gas}$ and $C_{gas}$ the gas displacement volume capacitance, i.e., the gas volume displaced by the flexing membrane in response to a voltage derived membrane displacement force, a type of mechanical and electrical resonance behavior will be observed. Thus, the flexible membrane capacitor viscosity sensor exhibits different impedances at frequencies below the referred to $R_{gas}C_{gas}$ resonance and above the $R_{gas}C_{gas}$ resonance with a significant change in impedance occurring for frequencies in the neighborhood of the referred to $R_{gas}C_{gas}$ "resonance." By measuring the change in the sensor impedance $Z_S(f)$ as a function of frequency f, frequency $f_{R'}$ at which the impedance exhibits the above described changes, can be easily identified and measured. Since the value of $f_R$ depends upon $R_{gas}$ which depends on gas viscosity, a measurement of $f_R$ provides a measurement of the viscosity $\eta$. The relationship between $f_R$ and $\eta$ can be calibrated using known reference gases. Since frequency can be measured very accurately using counting techniques this latter method of viscosity measurement (FIG. 9a) can provide a very accurate measurement of gas viscosity and a useful A/D method simultaneously.

Many methods for measuring f will be apparent to those skilled in the electronics arts upon reading this specification. One method is to use a voltage tunable oscillator and to sweep the oscillator (FIG. 9a) frequency with a ramp voltage V(t) and then to inspect the device's electrical response for the resonance. Another method is to use a feedback circuit to lock on the $R_{gas}C_{gas}$ resonance. Inspection of the relative phase between the applied oscillator voltage $V_{osc}(t)$ and the current from the sensor i(t) also provides a measurement of the resonance condition. All of the above features can be used to determine the fluid viscosity.

Refinements and variations of the flexible membrane capacitor viscosity sensor are possible. For example, the gas exit port and gas entrance port for the capacitor cavity can be separated with a valve placed at the gas entrance port to insure that the gas under measurement is not mixed with another gas. Here the exit port is sufficiently long that significant mixing with the ambient gas external to the sensor cavity does not occur during viscosity measurement.

Selection of gas port size 5 and port length selects the magnitude of the impedance to gas flow and thus also selects resonance $f_R$, decay time of C(t) and slope dC(t)/dt at t=0, etc. for a given gas viscosity.

The gas port 5 is both a gas conduit means and an impeding means to impede the flow of gas. Any impeding means may be used in the conduit which tends to impede or slow the flow of gas through the conduit.

The preferred embodiment of the present device is such that the membrane 1 and its surrounding supporting structure 2 are fabricated of silicon. Silicon has the advantage of having a readily available extensive and advanced technology for device batch processing with attendant integrated circuits inducted on the same substrate. The complementary substrate housing the gas cavity (capacitor cavity) and fixed capacity plate may be of any material including silicon although the present embodiment uses pyrex material for an insulating substrate 3. Viscosity measurement sensitivity of the device can be increased by decreasing the spacing between the two capacitor plates 2 and 8, and by making the area of capacitor plate 8 small compared to the conducting flexible membrane 1, and placing capacitor plate 8 directly beneath the center of the flexible membrane 1. Sensitivity is also increased by using a more flexible membrane which can be achieved in silicon by making the flexible membrane 1 thinner, the diameter or width and lengths of the membrane 1 larger, or by using a more flexible conducting membrane material 1.

Fabrication technology is well known to those skilled in the micromechanical silicon device art when silicon and pyrex are used, or when silicon and silica are used (silicon replacing pyrex). Silicon to silicon bonding is easily achieved using Indium and Indium alloys as a high temperature adhesive, or by using some other metal or alloy which will stick to $SiO_2$ and Si. $SiO_2$ insulation layers are easily grown on Si to provide suitable insulation where needed. A flexible capacitor plate of metal or of a conductive polymer is also feasible and is intended to be covered by the appended claims. A polymer to which has been added a conducting film can also be used.

Figure 9A:
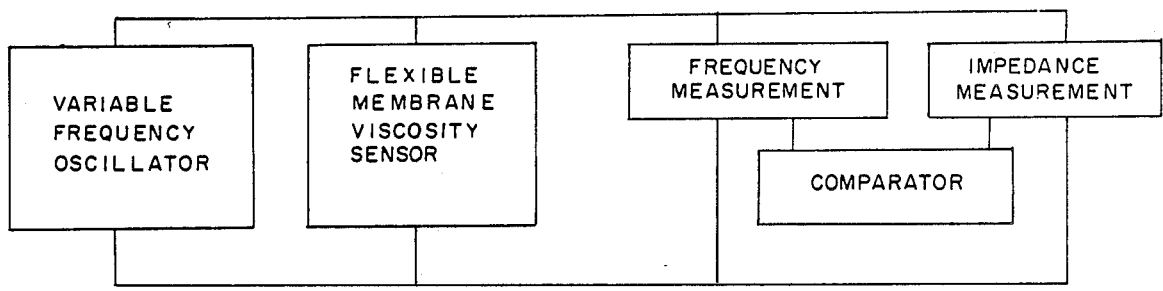
FIG. 9a is a schematic representation of the a.c. method of measuring viscosity using the flexible membrane capacitor viscosity sensor.
Figure 9B:
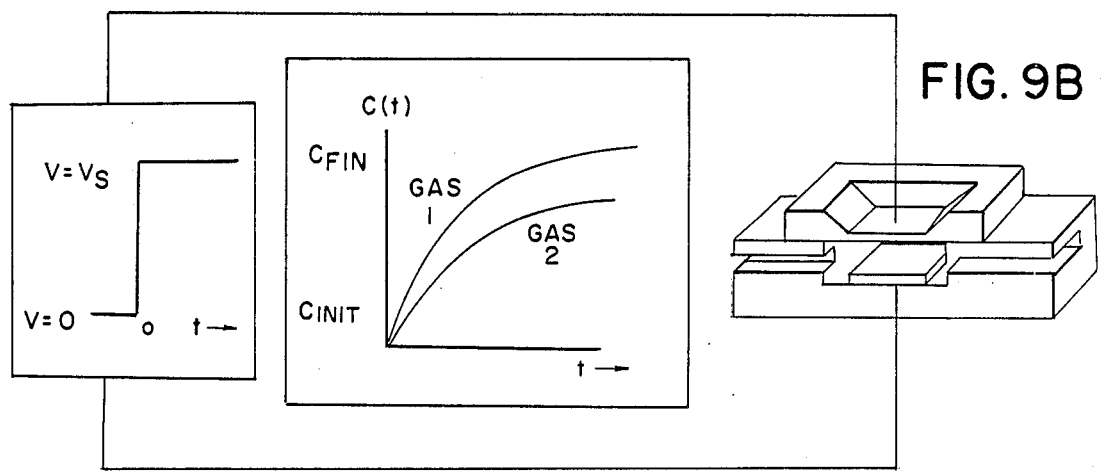
FIG. 9b is a block diagram, schematically representing the general circuit configuration for the flexible membrane viscosity sensor response to a step function voltage applied across the conducting plate of the capacitor.

FIG. 9a is a schematic representation of the a.c. method of measuring viscosity using the flexible membrane capacitor viscosity sensor. A variable frequency oscillator delivers an oscillating voltage (or current) to the sensor at frequency f, said frequency being variable. The impedance of the sensor has a frequency dependence which is a function of the viscosity of the fluid being subjected to a differential pressure by the flexible membrane. A resonance condition which has a characteristic frequency $f_{Res}$ which is viscosity dependent and which is exhibited in the measured frequency dependent a.c. impedance $Z_{meas}$ of the flexible membrane capacitor is measured to provide the value of the fluid's viscosity by inspecting $Z_{meas}(f)$ vs f.

In FIG. 9b the block diagram schematically represents the general circuit configuration for the flexible membrane viscosity sensor response to a step function voltage applied across the capacitor's conducting plates. The response time of the flexible membrane capacitance change from its initial value $C_{init}$ to its final value $C_{fin}$ is dependent upon the time required for the gas transfer between the capacitor value and the surroundings to occur. The viscosity is measured from the slope dC/dt at t=0 or from the characteristic time for C(t) to change or from the value of $C(t_o)$ at the same relative value of time $t_o$ for different fluids.

Figure 9C:
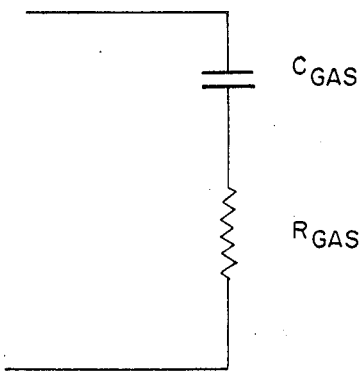
FIG. 9c is a simplified equivalent circuit representing the simplified fluid dynamics of the system.

In FIG. 9c a simplified equivalent circuit represents the simplified fluid dynamics of the system. Here $C_{vol}$ represents the fluid volume displaced by the flexible membrane and $R_{visc}$ represents the capacitor's resistance to fluid flow through the port between the capacitor fluid volume and surroundings. The capacitor's impedance is frequency dependent upon $C_{vol}$ and $R_{visc}$. $R_{visc}$ is dependent upon the viscosity of the fluid.

As an example: A typical sensor capacitor of the invention has a membrane about 2 microns thick etched from a wafer about 0.33 mm thick. The membrane is about 1 cm square. The fixed plate is a thin metal (al) film about 1 cm square and 0.1 micro thick. The gap between the plates 1 and 8 is typically 5 microns. A typical capacitance value is 100 pF which shows an approximately 5% change with applied d.c. voltage.

The fluid viscosity sensor may be used in any way which employs a capacitor with at least one relatively movable plate. The movable plates are electrically driven and an electrical measurement is taken remote from the plates in the driving circuit. The electrical measurement may be for example capacitance, average capacitance, change in capacitance and any of those measurement may be time differentiated. The electrical measurement may be frequency or phase displacement or other measurement. The electrical driving may be pulse, periodic pulse or an a.c. driving. The measuring and driving may be in combined or separated circuits. The fluid preferably contacts at least one movable conductor or at least tends to be moved by at least one movable conductor. One or both conductors may be movable. Plural movable conductors may be mounted in an array.

The fluid may be unconfined or partially confined or in a sealed volume adjacent the conductors.

The device can be fabricated in a number of different ways from different materials and of differing dimensions.

For example, the device can be micromachined from silicon and glass. A photolithic pattern can be transferred to a 3 inch diameter silicon wafer of about 16 mils (approximately 0.4 mm) thickness. The pattern is etched with E.D.P. etchant to define the membrane, and supporting die. The membrane thickness is controlled using E.D.P. etch stop technology by diffusing a high concentration layer of boron into the surface of the silicon wafer to a depth suitable for the membrane thickness needed as determined by the desired spring constant stiffness, and by etching away the silicon with E.D.P. except for the heavily doped boron, diffused thin boron region. The glass substrate can be similarly patterned using photoresist and photolithographic technology and etching the well into the glass substrate using a suitable glass etchant such as buffered hydrofluoric acid. The silicon and glass structures can be aligned visually or by using a mask aligner so that the membrane is appropriately aligned over the capacitor plate 8 and the membrane is over the cavity 6. The heavily doped boron membrane and pedestal surface on the cavity 6 side of the pedestal provide a conducting surface which together with the metallic plate forms the two plate capacitor structure. The glass and silicon can be bonded together using an adhesive or using high temperature anodic bonding. Alternatively, a suitable adhesive would be Crazy Glue of Indium or Indium alloy which at an elevated temperature can be made to adhere to another medium layer, to glass, $SiO_2$ and to silicon, the latter through alloying above the In/Si eutectic temperature.

The fixed capacitor plate can be of conducting aluminum or gold. The fixed plate can be vacuum deposited and then patterned and aligned using conventional photolithographic technology and etching technology such as is used in integrated circuit fabrication.

By using photo reduction and stepper techniques as are commonly used in the integrated circuit industry, an array of identical patterns of a mask can be fabricated, and a set of masks fabricated, such that an array of sensors can be simultaneously batch processed, as is done with integrated circuits.

The sensor array may be left as an array for measuring profiles. Or, the array may be partitioned into individual chips to provide many near identical sensors.

Alternative technologies and materials may be used to fabricate similar sensors. In particular, glass substrate may be replaced by a silicon substrate in order to match material thermal coefficients of expansion to reduce temperature induced effects.

Alternative technologies and materials include the use of metal rather than an insulator of silicon or polymer support membrane, etc.

An example of the dimensions of the components of the micromechanical flexible capacitor plate viscosity sensor are a square membrane of 1.0 cm×1.0 cm area and approximately 1.0 micron thickness. A 0.5 cm wide surrounding is about 0.4 mm thick. The support is placed above a block having a cavity of approximately 5.5 microns depth and an approximate capacitance of 100 pF. Typical applied step voltages for this example range from 0 to +10 V resulting in a 4.3% capacitance change for +10 V d.c. voltage applied. Typical entry exit ports are approximately 5.5 microns deep, 0.6 mm wide and approximately 1 cm in length. The bottom capacitor place is approximately 1 cm×1 cm square and fabricated from vapor deposited aluminum. The electrical interconnect to the aluminum capacitor plate was taken out through a side port for external electrical connection. Viscosity values for different gases, such as Argon, Helium, $N_2$, $O_2$, $H_2$ and mixtures of $N_2$ and $H_2$ are easily discriminated using the example device described above.

The absolute value of viscosity is achieved thorugh device calibration using known reference gases.

In a preferred embodiment of the invention a membrane transducer is driven to change volume of a gap which tends to move fluid through a conduit. The transducer is sensed to determine physical movement. The sensed physical movement is correlated with the driving to provide an indication of resistance to flow of the fluid, hence viscosity. The preferred way of sensing transducer movement is to sense positional change between two conductors. Preferably one conductor is fixed, and one is flexible or is mounted on a flexible membrane. Preferably the positional change is sensed by a change in capacitance. The transducer movement may be sensed by a change in resistance in a piezoresistive membrane or a piezoresistive layer in or on a membrane. Piezoresistive element means in the present context may be a coating, layer, doped or impregnated with a substance that changes resistance upon stretching, bending or squeezing or other application of force in either a predictable or repeatable way in which resistance change may be related to movement.

Alternatively movement of the transducer may be detected through a reflected light and a polarizing grid or in any other suitable way for detecting relatively small deflections.

While the invention has been described with reference to specific embodiments, modifications and variations of the invention may be made without departing from the scope of the invention which is defined in the following claims.

We claim:

1. Fluid viscosity sensor apparatus comprising a capacitor having first and second relatively movable conductors, means for moving at least one of the conductors in a fluid relative to the other conductor, means for sensing the moving and means for indicating fluid viscosity according to the movement.

2. The apparatus of claim 1 wherein the moving means comprises electrical driving means and wherein the sensing means comprises means for sensing an electrical characteristic.

3. The method of fluid viscosity sensing comprising electrically driving a capacitive transducer having a gap between conductive plates, changing volume of the gap as the transducer is driven, conducting fluid through the gap and impeding flow of the fluid, sensing the transducer response to the electrical driving, sensing transient response of the transducer and correlating transient response with the driving as an indication of a transient change in fluid flow, and indicating fluid viscosity as a function of the transient change.

4. The fluid viscosity sensing method of claim 3 wherein the electrical driving of the transducer comprises deflecting a flexible conducting membrane toward a fixed conducting plate.

5. The method of claim 4 wherein the conducting of fluid through the gap comprises conducting fluid through an etched conduit in a substrate and wherein the impeding of flow comprises impeding flow from the fluid out of the etched conduit through an etched impeding opening.

6. The fluid viscosity sensing method of claim 5 wherein the sensing comprises sensing impedance changes in electrical driving means which drives the transducer.

7. The fluid viscosity sensing method of claim 3 wherein the sensing comprises sensing resistance change in a piezoresistive element of the transducer.

8. The fluid viscosity sensing method of claim 3 wherein the electrical driving comprises periodically energizing the transducer.

9. The fluid viscosity sensing method of claim 8 further comprising modulating frequency of energizing the transducer and wherein the correlating comprises correlating transient response with the driving frequency.

10. The fluid viscosity sensing method of claim 3 wherein the electrical driving comprises driving the transducer with a single pulse and wherein the sensing transient response comprises sensing time of movement of the transducer.

11. Viscosity sensor apparatus comprising a transducer, electrical driving means connected to the transducer, a substrate connected to the transducer, the substrate having a recess means which is at least partially closed by the transducer, thereby forming a gap, conduit means connected to the recess means for conducting fluid to and from the gap and impeding means connected to the conduit means for impeding passage of the fluid in the conduit means, wherein when the transducer is energized by the driving means and volume of the gap is changed, and sensor means connected to the transducer for sensing time dependent response and for indicating viscosity of fluid in the gap.

12. The viscosity sensor apparatus of claim 1 wherein the sensor means is electrically connected for sensing electrical changes in the sensor means.

13. The viscosity sensor of claim 11 further comprising frequency modulation means connected to the electrical driving means for changing frequency of the driving of the transducer and wherein the sensor means is connected to the electrical driving means for sensing transient electrical change in the sensor means thereby indicating viscosity of fluid in the gap.

14. The viscosity sensor apparatus of claim 11 wherein the transducer comprises a first conductor supported above the recess and a second conductor supported in the recess.

15. The viscosity sensor apparatus of claim 14 wherein the first conductor is a first flexible conducting membrane and wherein the second conductor is a conducting plate fixed at the bottom of the recess, the conducting membrane and the conducting plate being separated by the gap.

16. The viscosity sensor apparatus of claim 15 wherein the recess means, the conduit means and the impeding means are etched within the substrate.

17. The viscosity sensor apparatus of claim 16 further comprising an electrical connector channel etched within the substrate and communicating with the recess and an electrical conductor positioned in the channel and connected to the conducting plate.

18. The viscosity sensor apparatus of claim 11 wherein the sensor means comprises impedance sensing means connected to electrical means for sensing time dependent impedance transient of the transducer.

19. The viscosity sensor apparatus of claim 11 wherein the transducer comprises a piezoresistive element and wherein the sensor comprises means for sensing resistance changes in the element.

20. The viscosity sensor apparatus of claim 11 wherein the driving means comprises means for providing a voltage step to the transducer, and wherein the sensor means comprises means for determining time dependent response of an electrical characteristic of the transducer and comprises means for converting the time dependent response to an indication of viscosity.

21. Fluid viscosity sensor apparatus comprising:
(a) a single capacitive transducer having a gap;
(b) electrical driving means connected to the transducer for electrically driving the transducer with periodic electrical pulses for periodically changing volume of the gap;
(c) fluid conduit means connected to the gap for conducting fluid to and from the gap;
(d) impeding means connected to the fluid conduit means for impeding flow of fluid in the conduit means;
(e) means for varying the energizing of the transducer;
(f) sensor means for sensing responses in the transducer to the energizing which are indicative of fluid flow through the conduit means and the impeding means;
(g) correlation means for correlating the driving and the response;
(h) conversion means for converting the correlation to an indication of viscosity; and
(i) indication means for indicating viscosity of fluid in the gap.

22. The fluid viscosity sensor apparatus of claim 21 wherein the transducer comprises first and second components, the first component comprising a flexible conducting membrane and the second component comprising an insulating substrate having a recess adjacent the membrane and a conductive plate positioned in the recess and separated from the membrane by a gap.

23. The fluid viscosity sensor apparatus of claim 22 wherein the conducting means are formed in the insulating substrate in communication with the recess and wherein the conduit means extend from the recess beyond the membrane and wherein the impeding means are formed in the substrate as openings of the conduit means in an external surface of the substrate.

24. The fluid viscosity sensor apparatus of claim 23 wherein the recess, conduit means and impeding means are etched in the substrate.

25. The fluid viscosity sensor apparatus of claim 24 wherein the sensor means senses change in capacitance between the conducting membrane and the plate.

26. The fluid viscosity sensor apparatus of claim 21 wherein the transducer includes a piezoresistive element and wherein the sensor means is connected to the element to sense change in resistance.

27. The fluid viscosity sensing apparatus of claim 21 wherein the driving means comprises means for providing voltage steps to the transducer and wherein the sensor means comprises means for determining time dependent response of the transducer.

* * * * *